US011998633B2

(12) United States Patent
Cho et al.

(10) Patent No.: US 11,998,633 B2
(45) Date of Patent: Jun. 4, 2024

(54) TOPICAL SOL-GEL COMPOSITION FOR THE TREATMENT OF DERMATITIS

(71) Applicant: Amorepacific Corporation, Seoul (KR)

(72) Inventors: Wonkyung Cho, Yongin-si (KR); Kwanghyun Shin, Yongin-si (KR); Joonho Choi, Yongin-si (KR); Kiwha Lee, Yongin-si (KR); Jong Hwa Roh, Yongin-si (KR); Miyoung Park, Yongin-si (KR); Youngho Park, Yongin-si (KR); Eunsil Park, Yongin-si (KR); Jaehong Park, Yongin-si (KR); Byoung Young Woo, Yongin-si (KR); Min Soo Kim, Yongin-si (KR); Eun Sol Ha, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 214 days.

(21) Appl. No.: 17/289,382

(22) PCT Filed: Oct. 16, 2019

(86) PCT No.: PCT/KR2019/013544
§ 371 (c)(1),
(2) Date: Apr. 28, 2021

(87) PCT Pub. No.: WO2020/096217
PCT Pub. Date: May 14, 2020

(65) Prior Publication Data
US 2022/0000775 A1    Jan. 6, 2022

(30) Foreign Application Priority Data
Nov. 9, 2018 (KR) .......................... 10-2018-0136973

(51) Int. Cl.
*A61K 9/08* (2006.01)
*A61K 9/06* (2006.01)
(Continued)

(52) U.S. Cl.
CPC ................ *A61K 9/06* (2013.01); *A61K 31/44* (2013.01); *A61K 47/10* (2013.01); *A61K 47/26* (2013.01);
(Continued)

(58) Field of Classification Search
CPC ........ A61K 9/06; A61K 9/0014; A61K 31/44; A61K 47/10; A61K 47/26; A61K 47/32; A61K 47/38
See application file for complete search history.

(56) References Cited

U.S. PATENT DOCUMENTS

| 5,658,919 A | 8/1997 | Ratnaraj et al. |
| 7,671,205 B2 | 3/2010 | Delong et al. |

(Continued)

FOREIGN PATENT DOCUMENTS

| KR | 10-2006-0060371 A | 6/2006 |
| KR | 10-2008-0076440 A | 8/2008 |

(Continued)

OTHER PUBLICATIONS

Zhao et al. Characterisation of the interactive properties of microcrystalline cellulose-carboxymethyl cellulose hydrogels. International Journal of Pharmaceutics 415 (2011) 95-101. (Year: 2011).*

(Continued)

*Primary Examiner* — Kevin S Orwig
*Assistant Examiner* — K. A. Ketcham
(74) *Attorney, Agent, or Firm* — Sughrue Mion, PLLC

(57) ABSTRACT

One aspect of the present disclosure relates to a sol-gel composition enabling reversible sol-gel transition and, more specifically, to a sol-gel composition of which the viscosity changes by external physical force so that reversible sol-gel transition is performed.

5 Claims, 1 Drawing Sheet

(51) Int. Cl.
  A61K 31/44   (2006.01)
  A61K 47/10   (2017.01)
  A61K 47/26   (2006.01)
  A61K 47/32   (2006.01)
  A61K 47/38   (2006.01)
  A61K 9/00    (2006.01)

(52) U.S. Cl.
  CPC ............... A61K 47/32 (2013.01); A61K 47/38 (2013.01); A61K 9/0014 (2013.01)

(56) References Cited

U.S. PATENT DOCUMENTS

| | | |
|---|---|---|
| 2007/0298106 A1 | 12/2007 | Park et al. |
| 2008/0014275 A1 | 1/2008 | Buehler et al. |
| 2008/0312234 A1 | 12/2008 | Kim et al. |
| 2010/0136119 A1 | 6/2010 | Park |
| 2010/0144896 A1 | 6/2010 | Hahn et al. |
| 2011/0015230 A1 | 1/2011 | Shin et al. |
| 2013/0210868 A1 | 8/2013 | Cui et al. |
| 2017/0290747 A1* | 10/2017 | Bouarfa et al. .......... A61K 8/04 |
| 2017/0342027 A1 | 11/2017 | Woo et al. |

FOREIGN PATENT DOCUMENTS

| | | |
|---|---|---|
| KR | 10-2008-0076667 A | 8/2008 |
| KR | 1020080076667 * | 8/2008 |
| KR | 10-2009-0033916 A | 4/2009 |
| KR | 10-2009-0040335 A | 4/2009 |
| KR | 10-2010-0119757 A | 11/2010 |
| KR | 10-2016-0101554 A | 8/2016 |
| KR | 10-2017-0042548 A | 4/2017 |
| KR | 10-2017-0081315 A | 7/2017 |
| WO | 2005/115353 A1 | 12/2005 |
| WO | 2006/050301 A2 | 5/2006 |
| WO | 2016/087952 A1 | 6/2016 |

OTHER PUBLICATIONS

Yun et al. TRPV1 antagonist can suppress the atopic dermatitis-like symptoms by accelerating skin barrier recovery J Dermatol Sci. Apr. 2011; 62(1):8-15. (Year: 2011).*

G. H. Zhao et at., "Characterisation of the interactive properties of microcrystalline cellulose-carboxymethyl cellulose hydrogels", International Journal of Pharmaceutics, 2011, pp. 95-101, v415.

International Searching Authority, Written opinion for PCT/KR2019/013544 dated Jan. 10, 2001.

International Searching Authority, International search report for PCT/KR2019/013544 dated Jan. 10, 2001.

Korean Office Action issued Jan. 11, 2024 in Application No. 10-2018-0136973.

Moji Christianah Adeyeye, et al., "Viscoelastic Evaluation of Topical Creams Containing Microcrystalline Cellulose/Sodium Carboxymethyl Cellulose as Stabilizer," AAPS Tech, 2002, vol. 3, No. 2, Article 8, pp. 1-10 (10 pages total).

* cited by examiner

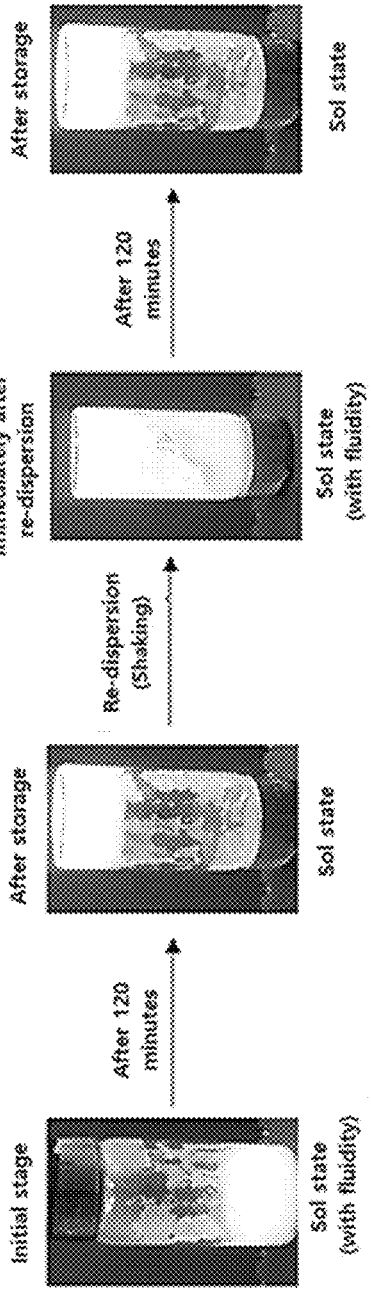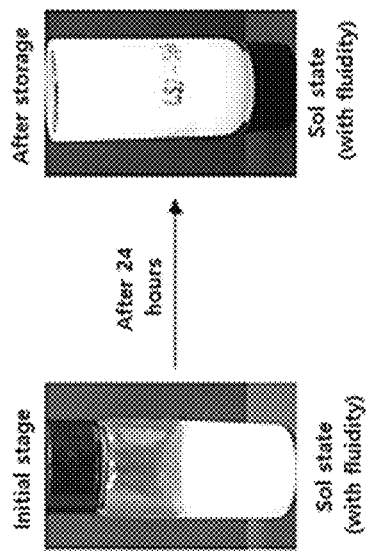

TOPICAL SOL-GEL COMPOSITION FOR THE TREATMENT OF DERMATITIS

CROSS REFERENCE TO RELATED APPLICATIONS

This application is a national stage entry application of PCT/KR2019/013544 filed on Oct. 16, 2019, which claims the benefit of priority based on Korean Patent Application No. 10-2018-0136973 filed on Nov. 9, 2018, the entire contents of which are incorporated herein by reference.

TECHNICAL FIELD

One aspect of the present disclosure is relates to a sol-gel composition enabling reversible sol-gel transition and, more specifically, to a sol-gel composition of which the viscosity changes by physical force applied from the outside so that reversible sol-gel transition is performed.

BACKGROUND ART

Among the commercially available drugs, there are hydrophilic drugs that are well soluble in water, but most drugs, including anticancer drugs, are poorly soluble drugs with very low solubility in water due to the properties of their molecular structure. These poorly soluble drugs are difficult to be absorbed into the body, and thus there is a problem that the therapeutic efficacy is reduced, and when applied as an injection, these poorly soluble drugs have serious side effects that may form blood clots.

Accordingly, the development of hydrogels that can increase the solubility of the poorly soluble drugs and efficiently deliver them into the body is actively progressing.

A hydrogel is a three-dimensional structure consisting of a network of hydrophilic polymers, and 90% or more of its constituents are composed of moisture. Since the hydrogel has properties similar to living tissues such as high moisture content, porous structure, relatively soft physical properties, and biocompatibility, the hydrogel is being actively studied in the biomedical field or cosmetic field.

In addition, the hydrogel can exhibit various properties depending on which polymer is selected as the main chain or on which crosslinking method is selected. For example, when using a stimuli-responsive polymer, a hydrogel that responds to a specific stimulus can be formed. If a polymer having a lot of ionizing functional groups is used, a hydrogel whose physical properties can be changed due to a change in pH can be formed, and if a polymer that undergoes structural modification by a specific stimulus such as temperature or light is used, a hydrogel whose physicochemical behavior changes in response to the stimulus can be formed. In addition, if a material containing asymmetric particles and capable of forming a loose three-dimensional structure through various contact points is used, a hydrogel whose viscosity changes by the physical force applied from the outside can be formed. These stimulation-sensitive hydrogels exhibit a phenomenon of sol-gel transition depending on the corresponding stimulation.

On the other hand, in the case of pharmaceutical and pharmacological suspension, there may be problems in the stability of the formulation due to separation of layers (caking, sedimentation) during storage, and in the case of syrup, there is a risk of spillage of the drug from the metering device during metering and oral administration, due to the low viscosity and the physical force exerted on the metering device (spoon, etc.). For example, in the case of a patient with motility disorder (hand trembling caused by limb trembling, hand tremor, and lack of control of micromotion) or a pediatric patient with fear of taking a drug, it is very difficult to measure or take an accurate dosage using a metering device.

As a result, it is necessary to develop a composition enabling sol-gel transition, which is possible to make a sol-gel transition by the change of viscosity by external physical force at isothermal temperature, improves the stability of the suspension by controlling the viscosity, facilitates metering of the drug to be administered, increases the solubility of poorly soluble drugs and can be efficiently delivered to the body.

In addition, the technology to control the flowability of the formulation in the cosmetic field is one of the technologies that have been continuously exploited and developed. The reason why it is important to control the flowability in cosmetics is that in the storage state before application, it has low flowability, but changes into a fluid with high flowability as friction is applied during application, and again, when the friction is extinguished, the flowability is lost and various functions as cosmetics can be exhibited.

Likewise, in general, the resistance felt by hands and skin when applying cosmetics to the skin is pointed out as a negative factor such as stiffness and stuffiness. After all, ease of application when applied to the skin is recognized as one of the important factors determining the quality of cosmetics.

Accordingly, it is necessary to develop a composition with improved ease of application, wherein the viscosity of the composition changes by physical force applied from the outside at isothermal temperature so that sol-gel transition is performed.

DISCLOSURE

Technical Problem

In order to solve the above problems, the present inventors have prepared a composition whose viscosity changes by physical force applied from the outside at isothermal temperature so that sol-gel transition is performed, and have confirmed that the composition exhibits a high viscosity in the form of a gel to prevent sedimentation of particles during storage, and is, when used, transformed into a low viscosity in the form of a sol by shaking it so that it can be easily measured and spread well and so on, and thus has ease of application, and additionally, can increase the solubility of poorly soluble drugs to form a hydrogel that can be efficiently delivered to the body, thereby completing one aspect of the present disclosure.

Accordingly, it is an object of one aspect of the present disclosure to provide a composition enabling convenient sol-gel transition while maintaining stability during storage.

Technical Solution

In order to achieve the above object, according to an example of one aspect of the present disclosure, a sol-gel composition comprising the first component of microcrystalline cellulose/carboxymethylcellulose sodium; the second component which is any one selected from hydroxypropyl methylcellulose (HPMC), polyvinylpyrrolidone vinyl acetate (PVP VA), and a mixture thereof; and the third component which is any one selected from Poloxamer, Polysorbate and a mixture thereof is provided.

Advantageous Effects

The composition enabling sol-gel transition according to one aspect of the present disclosure can prevent sedimentation of particles to maintain stability during storage, and when using it, it is easy to measure by physical force and the ease of application can be improved, by changing the viscosity by physical force applied from the outside at isothermal temperature and thus causing sol-gel transition.

In addition, the composition enabling sol-gel transition according to one aspect of the present disclosure may be formulated in the form of a suspension which can be efficiently delivered to the body by increasing the solubility of poorly soluble drugs.

DESCRIPTION OF DRAWINGS

FIG. 1 is an image obtained by photographing the phenomenon of sol-gel transition for suspensions of Example 1 and Comparative Example 1.

BEST MODE

The term "sol-gel composition" as used in one aspect of the present disclosure refers to a composition representing the characteristic of reversible sol-gel transition due to a change in viscosity by physical force applied from the outside.

The sol-gel composition according to an example of one aspect of the present disclosure comprises the first component of microcrystalline cellulose/carboxymethylcellulose sodium (microcrystalline cellulose and carboxymethylcellulose sodium); the second component which is any one selected from hydroxypropyl methylcellulose (HPMC), polyvinylpyrrolidone vinyl acetate (PVP VA), and a mixture thereof; and the third component which is any one selected from Poloxamer, Polysorbate and a mixture thereof.

The sol-gel composition means that it is a composition enabling sol-gel transition, the sol-gel transition is reversible, and the viscosity is changed by physical force applied from the outside at an isothermal temperature, and thus the sol-gel transition occurs. More specifically, when left without a physical force applied (static state), the composition becomes a gel state while colloidal particles have anisotropy and are loosely bonded to each other by the bonding force between the particles to give firmness. In addition, when applying a physical force, while the contact point is destroyed and the particles are arranged and thus the structure starts to be destroyed, as the viscosity is lowered, the composition changes to a sol state, and then after a certain period of time, as the viscosity is increased and the composition changes to a gel state again.

In addition, in the sol-gel composition according to one aspect of the present disclosure, in the case of a sol state, the viscosity is 5000 cp or less, and in the case of a gel state, it means that the viscosity is 50000 cp or more. The 'gel state' refers to a state in which the sol-gel composition does not flow downward when the container is turned upside down after placing the sol-gel composition according to one aspect of the present disclosure in a container.

Since the composition according to one aspect of the present disclosure is capable of sol-gel transition, it has good fluidity when it is in a sol state, so it is easy to measure, and it is easy to apply, so it is convenient to handle, and also, during storage, it may be possible to ensure the stability of the formulation by preventing sedimentation of the particles in a gel state.

The microcrystalline cellulose/carboxymethyl cellulose sodium, which is the first component, plays a role in representing the characteristics of the sol-gel transition.

The microcrystalline cellulose/carboxymethyl cellulose sodium, which is the first component, means that it is composed of 82 to 89% of microcrystalline cellulose and 11 to 18% of carboxymethyl cellulose sodium.

The first component may be contained in an amount of 1 to 10 wt. %, preferably 2 to 8 wt. %, and more preferably 4 to 6 wt. %, based on the total weight of the composition, but limited thereto.

If the first component is less than 1 wt. % based on the total weight of the composition, the sol-gel transition may not be possible or the gel may not be formed or layer separation may occur even after a long period of time elapses in a static state. On the other hand, if the first component exceeds 10 wt. % based on the total weight of the composition, the composition has a high viscosity and is unsuitable for use as a pharmaceutical composition and the reversible sol-gel transition of the composition may not occur or it may take a long time to form a gel from the sol.

When mixed with a drug or an active ingredient, the second component may encapsulate them or be mixed with them to increase the solubility in an aqueous solution. By incorporating the second component into the composition according to one aspect of the present disclosure, it is possible to increase the delivery rate and increase biocompatibility and bioaffinity in delivering drugs or active ingredients into the body.

The second component may be used to uniformly distribute the first component.

The second component is any one selected from hydroxypropyl methylcellulose, polyvinylpyrrolidone vinyl acetate, and mixtures thereof, preferably hydroxypropyl methylcellulose or polyvinylpyrrolidone vinyl acetate, more preferably polyvinylpyrrolidone vinyl acetate, but is not limited thereto.

The second component may be contained in an amount of 0.01 to 5 wt. %, preferably 0.1 to 2 wt. %, more preferably 0.5 to 1 wt. %, based on the total weight of the composition, but is not limited thereto.

If the second component is less than 0.01 wt. % based on the total weight of the composition, the sol-gel transition may not be possible or the gel may not be formed even after a long period of time elapses in a static state. On the other hand, if the second component exceeds 5 wt. %, the composition has a high viscosity and is unsuitable for use as a pharmaceutical composition and the reversible sol-gel transition of the composition may not occur.

The third component is a surfactant of the composition, which has hydrophilic molecules and hydrophobic molecules simultaneously so that poorly soluble drugs can be dissolved in an aqueous solution, and hydrophobic substances and hydrophilic substances are well dispersed to form colloidal particles. Accordingly, the third component may serve to uniformly disperse poorly soluble drugs or the first component.

The third component is any one selected from Poloxamer, Polysorbate, and mixtures thereof, preferably Poloxamer or Polysorbate, but is not limited thereto.

The Polysorbates are polyoxyethylene higher aliphatic alcohols produced by binding ethylene oxide to sorbitan fatty acid esters, and may have different roles depending on the number of polyoxyethylene groups and differences in fatty acids.

The Polysorbate may be any one selected from Polysorbate 20, Polysorbate 60, Polysorbate 80, and combinations thereof.

The third component may be contained in an amount of 0.01 to 5 wt. %, preferably 0.05 to 2 wt. %, more preferably 0.1 to 1 wt. %, based on the total weight of the composition, but is not limited thereto.

If the third component is less than 0.01 wt. % based on the total weight of the composition, the colloidal particles cannot be formed and layer separation may occur. On the other hand, if the third component exceeds 5 wt. %, the sol-gel transition may not be possible or the gel may not be formed even after a long period of time elapses in a static state.

The sol-gel composition according to one aspect of the present disclosure further comprises polyol, so that drugs or active ingredients can be easily wetted in the hydrogel composition, and biocompatibility can be improved. In addition, it is possible to form a sol or gel having a soft texture.

The polyol may be at least one selected from the group consisting of propylene glycol, glycerin, butylene glycol, polyethylene glycol, polypropylene glycol, dipropylene glycol, pentylene glycol and sorbitol, preferably any one selected from propylene glycol, glycerin and a mixture thereof, more preferably a mixture of propylene glycol and glycerin, but is not limited thereto.

The polyol may be contained in an amount of 0.1 to 20 wt. %, preferably 0.5 to 15 wt. %, and more preferably 1 to 10 wt. %, based on the total weight of the composition, but is not limited thereto.

If the polyol is less than 0.1 wt. %, based on the total weight of the composition, the drugs or active ingredients may not be wetted in the hydrogel. If the polyol exceeds 20 wt. %, the sol-gel transition may not be possible or the texture of the sol or gel may not be smooth.

The sol-gel composition according to one aspect of the present disclosure may further comprises preservative to increase the chemical stability of drugs or active ingredients, and also to prevent decomposition or change due to changes in the external environment in the process of distributing the sol-gel composition.

The preservative may be at least one selected from the group consisting of phenoxyethanol, 1,2-hexanediol, 1,3-propanediol, methyl propanediol, 1,2-pentanediol, 1,2-octanediol, 1,2-decanediol, 1,5-pentanediol, 1,6-hexanediol, 1,8-octanediol, 1,2-decanediol, ethylhexylglycerin, hexoxypropan-1,2-diol, heptoxy-propan-1,2-diol, octoxy-propan-1,2-diol, 3-phenoxy-propan-1,2-diol, 3-benzyloxy-propan-1,2-diol, 3-phenylethyloxy-propan-1,2-diol, 3-phenylpropyloxy-propan-1,2-diol, 3-methylbenzyloxy-propan-1,2-diol, sorbitan caprylate, triclosan, climbazole, Octopirox (1-hydroxy-4-methyl-6-(2,4,4-trimethylpentyl)-2 (1H)-pyridone, 2-aminoethanol), chitosan, farnesol, 2-butyloctanoic acid, 2-benzylheptan-1-al, glycerol monolaurate, bis(2-pyridylthio)zinc 1,1'-dioxide, N,N'-(decane-1,10-diyl-dipyridin-1-yl-4-ylidene)-dioctan-1-amine dihydrochloride (octenidine dihydrochloride), thymol, eugenol, benzyl alcohol, 2-phenyethyl alcohol, 3-phenyl propanol, 1-phenoxypropan-2-ol, 3-phenoxypropanol, and benzyloxymethanol, preferably phenoxyethanol, but is not limited thereto.

The preservative may be contained in an amount of 0.01 to 1 wt. %, preferably 0.1 to 1 wt. %, more preferably 0.2 to 0.5 wt. %, based on the total weight of the composition, but is not limited thereto.

The sol-gel composition according to one aspect of the present disclosure is capable of sol-gel transition wherein the gel may be a hydrogel, and the hydrogel refers to a three-dimensional structure of a hydrophilic polymer that holds a sufficient amount of moisture. Therefore, the sol-gel composition may be in the form of a hydrogel expanded by absorbing the moisture in the presence of moisture.

The sol-gel composition according to one aspect of the present disclosure may be formed of colloidal particles. In this case, the size of the particles may be 1 to 100 μm, preferably 1 to 10 μm, and more preferably 2 to 6 μm, but is not limited thereto. If the size of the colloidal particles is less than 1 μm, it may be difficult to form a gel, and since leaching is easy, it is difficult to exhibit a sustained release pattern of the drug. On the other hand, if the size of the colloidal particles exceeds 100 μm, separation of layers or sedimentation of particles may occur.

In addition, the size of the colloidal particles may be adjusted by controlling the concentration or content of the second component and the third component.

On the other hand, the sol-gel composition further comprises a bioactivity material to further improve the delivery rate and biocompatibility of drugs or active ingredients in the body in the treatment, cure, prevention or diagnosis of diseases, or in use in cosmetics. Examples of the bioactivity material may comprise proteins or peptides, nucleic acids, extracellular matrix materials, and drugs with medicinal therapeutic functions such as cells, growth factors and hormones. In addition, when the composition changes to a gel or hydrogel, in order to be prepared to contain the bioactivity material, the bioactivity material may be prepared to be contained in one solution, and then mixed with another solution, thereby synthesizing the gel or the hydrogel. In this case, the bioactivity material is in a form supported in the gel or hydrogel formed. In addition, by mixing two solutions containing the bioactivity material in a syringe and delivering it to the diseased or wounded area using the syringe, it is possible to induce the manufacture of the gel or hydrogel containing the bioactivity material over time. Therefore, the composition of one aspect of the present disclosure is capable of sol-gel transition and thus can be used as a bioactivity material carrier, a cell carrier, or a drug carrier. In addition, the composition of one aspect of the present disclosure can be used as a tissue engineered supporter or cell therapeutics.

Examples of the drug as the bioactivity material may be antibiotics, anticancer agents, anti-inflammatory analgesics, antiviral agents, and antibacterial agents. Examples of the antibiotics may be selected from derivatives of tetracycline, minocycline, doxycycline, ofloxacin, levofloxacin, ciprofloxacin, clarithromycin, erythromycin, cefaclor, cefotaxime, imipenem, penicillin, gentamicin, streptomycin, vancomycin and the like and a mixture thereof. Examples of the anticancer agents may be an anticancer agent selected from derivatives of methotrexate, carboplatin, taxol, cis-platin, 5-fluorouracil, doxorubicin, etoposide, paclitaxel, camptothecin, cytosine arabinose and the like and a mixture thereof. Examples of the anti-inflammatory agents may be an anti-inflammatory agent selected from derivatives of indomethacin, ibuprofen, ketoprofen, piroxicam, flurbiprofen, diclofenac and the like and a mixture thereof. Examples of antiviral agents may be an antiviral agent selected from derivatives of acyclovir, lovabin and the like and a mixture thereof. Examples of antimicrobial agents may be an antimicrobial agent selected from derivatives of ketoconazole, itraconazole, fluconazole, amphotericin-B, griseofulvin and the like and a mixture thereof.

In an example of one aspect of the present disclosure, the composition may contain a drug, makes it possible to precisely control the amount of the drug to be administered into the body by using the phenomenon of sol-gel transition, and can prevent the sedimentation of particles in storing the drug to have the stability of the formulation.

As an example, the composition may be provided as a pharmaceutical composition comprising a therapeutic agent for seborrheic dermatitis. At this time, a representative example of the therapeutic agent for seborrheic dermatitis may be (R)—N-[1-(3,5-difluoro-4-methansulfonylaminophenyl)-ethyl]-3-(2-propyl-6-trifluoromethyl-pyridin-3-yl)-acrylamide.

In addition, examples of the proteins or peptides that can be contained in the composition and can be delivered into a living body may be various biologically active peptides such as hormone, cytokine, enzyme, antibody, growth factor, transcriptional regulatory factor, blood factor, vaccine, structural protein, ligand protein, polysaccharide and receptor, cell surface antigen, and receptor antagonist, and derivatives and analogs thereof, which are used to treat or prevent diseases. Specifically, bone growth factor, hepatic growth hormone, growth hormone releasing hormone and peptide, interferons and interferon receptors (e.g. interferon-alpha, -beta and -gamma, water soluble type I interferon receptor, etc.), granulocyte colony stimulating factor (G-CSF), granulocyte-macrophage colony stimulating factor (GM-CSF), glucagon-like peptides (GLP-1, etc.), G-protein-coupled receptor, interleukins (e.g. interleukin-1, -2, -3, -4, -5, -6, -7, -8, -9, etc.) and interleukin receptors (e.g., IL-1 receptor, IL-4 receptor, etc.), enzymes (e.g. glucocerebrosidase, iduronate-2-sulfatase, alpha-galactosidase-A, agalsidase alpha or -beta, alpha-L-iduronidase, chitinase, butyrylcholinesterase, lipase, glutamate decarboxylase, imiglucerase, uricase, platelet-activating factor acetylhydrolase, neutralendopeptidase, myeloperoxidase, etc.), interleukin and cytokine binding proteins (e.g. IL-18 bp, TNF-binding protein, etc.), macrophage activating factor, macrophage peptide, B cell factor, T cell factor, protein A, suppressive factor of allergy, tumor necrosis factor (TNF) alpha inhibitory factor, cell necrosis glycoprotein, immunotoxin, lymphotoxin, tumor necrosis factor, tumor inhibitory factor, transforming growth factor, alpha-1 antitrypsin, albumin, alpha-lactalbumin, apolipoprotein-E, erythropoietin, hyperglycosylated erythropoietin, angiopoietin, hemoglobin, thrombin, thrombin receptor activating peptide, thrombomodulin, blood factor, blood factor a, blood factor XIII, plasminogen activator, fibrin-binding peptide, urokinase, streptokinase, hirudin, protein C, C-reactive protein, renin inhibitor, collagenase inhibitor, superoxide dismutase, leptin, platelet derived growth factor, epithelial cell growth factor, epidermal growth factor, angiostatin, angiotensin, bone morphogenic protein, osteogenesis promoting protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors (e.g. nerve growth factor, cilliary neurotrophic factor, axogenesis factor-1, brain-natriuretic peptide, glial derived neurotrophic factor, netrin, neurophil inhibitor factor, neurotrophic factor, neuturin, etc.), parathyroid hormone, relaxin, secretin, somatomedin, insulin-like growth factor, adrenocortical hormone, glucagon, cholecystokinin, pancreatic polypeptide, gastrin-releasing peptide, corticotropin releasing factor, thyrotrophin, autotaxin, lactoferrin, myostatin, receptors (e.g. TNFR(P75), TNFR(P55), IL-1 receptor, VEGF receptor, B cell activating factor receptor, etc.), receptor antagonist (e.g. IL1-Ra, etc.), cell surface antigen (e.g. CD 2, 3, 4, 5, 7, 11a, 11b, 18, 19, 20, 23, 25, 33, 38, 40, 45, 69, etc.), monoclonal antibody, polyclonal antibody, antibody fragments (e.g. scFv, Fab, Fab', F(ab')2 and Fd), virus derived vaccine antigen and the like can be exemplified.

Examples of the nucleic acid that can be physically supported on the composition or chemically bound to be delivered into a living body may be DNA, RNA, PNA, oligonucleotides, and the like.

Examples of the extracellular matrix material that can be physically supported in the composition or chemically bound to be delivered into a living body may be collagen, fibronectin, gelatin, laminin, vitronectin, and the like.

Examples of the cell that can be physically supported in the composition or chemically bound to be delivered into a living body may be stem cells, fibroblasts, vascular endothelial cells, smooth muscle cells, nerve cells, cartilage cells, bone cells, skin cells, Schwann cells, and the like.

In an example of one aspect of the present disclosure, the composition can be used as a pharmaceutical composition.

In an example of one aspect of the present disclosure, the pharmaceutical composition means a composition administered for a specific purpose.

In addition, the pharmaceutical composition may further include a protein and a pharmaceutically acceptable carrier, excipient or diluent depending on the purpose of treatment.

The above "pharmaceutically acceptable" carrier or excipient means those approved by the regulatory department of the government, or means those approved by the government for use in vertebrates, more particularly humans, or those listed in other generally approved pharmacopeias.

In order to be suitable for parenteral administration, the pharmaceutical composition may be in the form of a suspension, solution or emulsion in an oily or aqueous carrier, and may be prepared in solid or semi-solid form and may contain formulation agents such as suspending agents, stabilizers, solubilizing agents and/or dispersants. This form can be sterilized and can be liquid. It can be stable under the conditions for manufacture and storage and can be preserved against the contaminating action of microorganisms such as bacteria and fungi. Alternatively, the pharmaceutical composition may be in the form of a sterile powder for reconstitution with an appropriate carrier prior to use. The pharmaceutical composition may be in unit-dose form, or may be present in microneedle patches, in ampoules, or in other unit-dose containers, or in multi-dose containers. In addition, the pharmaceutical composition can be stored in a lyophilized (freeze-dried) state which only requires the addition of a sterile liquid carrier, for example water for injection, just prior to use. Immediate injection solutions and suspensions can be prepared as sterile powders, granules or tablets.

In some non-limiting embodiments, the pharmaceutical composition of one aspect of the present disclosure may be formulated as a liquid, or may be contained in the form of microspheres in the liquid. In certain non-limiting embodiments, the pharmaceutical composition of one aspect of the present disclosure contains a pharmaceutically acceptable compound and/or mixture, which is an active ingredient of one aspect of the present disclosure, at a concentration between 0.001 and 100,000 U/kg. Also, in certain non-limiting embodiments, the excipient suitable for the pharmaceutical composition of one aspect of the present disclosure comprises preservatives, suspending agents, stabilizers, dyes, buffers, antimicrobial agents, antifungal agents, and isotonic agents such as sugar or sodium chloride. As used herein, the term "stabilizer" refers to a compound optionally used in the pharmaceutical composition of one aspect of the present disclosure to increase shelf life. In a non-limiting embodiment, the stabilizer may be a sugar, an amino acid, or a polymer. In addition, the pharmaceutical composition may include one or more pharmaceutically acceptable carriers. The carriers may be solvents or dispersed culture media. Non-limiting examples of the pharmaceutically acceptable carriers comprise water, saline, ethanol, polyols (e.g. glycerol, propylene glycol, and liquid polyethylene glycol), an oil, and a suitable mixture thereof. In addition, the parenteral formulation can be sterilized. Non-limiting examples of sterilization techniques comprise filtration through a bacteria-inhibiting filter, terminal sterilization, incorporation of a sterile preparation, irradiation, irradiation with sterilization gas, heating, vacuum drying, and freeze-drying.

In addition, the pharmaceutical composition may be a suspension formulation to increase stability and completeness of the formulation by dispersing drugs or active ingredients.

In one example of one aspect of the present disclosure, the term "administration" refers to a process of introducing the composition of one aspect of the present disclosure to a patient in any suitable manner. The composition of one aspect of the present disclosure may be administered through any conventional route to be applied to a target tissue. The composition of one aspect of the present disclosure can be administered through any general route as long as it can reach the target tissue. The pharmaceutical composition may be administered orally, intraperitoneally, intravenously, intramuscularly, subcutaneously, intradermally, intranasally, by intrapulmonary, intrarectally, intravitreally, intraperitoneally, or by intradural, or may be administered by application to the skin or to the mucous membrane.

One aspect of the present disclosure can provide a treatment method using the pharmaceutical composition, which may comprise administering the pharmaceutical composition in a pharmaceutically effective amount. In one aspect of the present disclosure, an effective amount may be controlled depending on various factors such as disease type, the severity of disease, the type and content of active and other ingredients contained in the composition, formulation type, the age, body weight, general health status, sex and diet of a patient, the time and route of administration, secretion rate of the composition, treatment period, and co-administered drug.

The sol-gel composition according to one aspect of the present disclosure can be used as a cosmetic composition. As an example, by shaking the container containing the composition, measuring the composition in a flowable sol state, and applying it to the skin, the composition becomes a gel state over time and thus the composition applied to the skin does not fly to the outside and the cosmetic effect can be sustained. In addition, the composition of one aspect of the present disclosure has good spreadability and can increase user satisfaction by forming a gel having a soft texture after being applied.

In this case, the cosmetic composition may be formulated in the form of emollient toilet water, nourishing toilet water, nourishing lotion, massage cream, nourishing cream, pack, gel, body lotion, body cream, body oil and body essence, but is not limited thereto. In each formulation, other ingredients other than the above essential ingredients may be appropriately selected and blended by a person skilled in the art without difficulty depending on the purpose of use.

One aspect of the present disclosure provides a method for producing the sol-gel composition according to one aspect of the present disclosure. Specifically, the method is a method of preparing a composition enabling sol-gel transition comprising the first component, the second component, and the third component, which comprises the steps of, S1) dissolving the first component, the second component, and the third component in a solvent, S2) adding a drug, and S3) stirring and dispersing for a period of time.

The order of the method for preparing the sol-gel composition according to one aspect of the present disclosure is particularly important in the case of applying poorly soluble drugs, and it is possible to easily disperse the drug by performing the steps S1), S2) and S3) in order.

The order of dissolving the first component, the second component, and the third component in the solvent in step S1) can be changed depending on their respective physical property, and it is preferable to dissolve the second component and the third component and then add the first component, but is not limited thereto.

Since the drug in step S2) is the same as previously described, a description thereof will be omitted.

The term "a period of time" as used in step S3) means 10 minutes to 24 hours, preferably 10 minutes to 2 hours, more preferably 1 hour, but is not limited thereto.

In addition, the method for preparing the composition enabling sol-gel transition according to one aspect of the present disclosure is all carried out under an isothermal condition and a condition in which humidity is kept constant, and preferably carried out at room temperature. At this time, the room temperature means 15 to 25° C.

Hereinafter, preferred examples are presented to aid in understanding one aspect of the present disclosure. However, the following examples are only illustrative of one aspect of the present disclosure, and it is obvious to those skilled in the art that various changes and modifications are possible within the scope of one aspect of the present disclosure and the scope of the technical idea, and also it is natural that such changes and modifications belong to the appended claims.

Preparation Example 1: Preparation Method of Suspension Composition

As shown in Table 1 below, Example 1 was prepared by first dissolving the second component and the third component in water, and then adding the first component and dispersing it, and then adding the drug and stirring for 1 hour to evenly disperse it. Meanwhile, Examples 2 to 9 were prepared by dissolving the second component and the third component in water, and adding the first component and dispersing it, and then adding the polyol and the preservative, and then adding the drug and stirring for 1 hour to evenly disperse it.

In addition, Comparative Example 1, as shown in Table 1 below, was prepared by dissolving the second component and the third component in water without the first component, and then adding the drug and stirring for 1 hour.

TABLE 1

| Item | Component | Comparative Example 1 wt. %) | Example 1 wt. %) | Example 2 wt. %) | Example 3 wt. %) | Example 4 wt. %) |
|---|---|---|---|---|---|---|
| Drug | (R)-N-[1-(3,5-difluoro-4-methansulfonylamino-phenyl)-ethyl]-3-(2-propyl-6-trifluoromethyl-pyridin-3-yl)-acrylamide | 1 | 1 | 1 | 1 | 1 |
| First component | Microcrystalline cellulose/ Carboxymethylcellulose sodium | — | 4 | 4 | 4 | 4 |
| Second component | Hydroxypropyl methylcellulose | — | — | 0.5 | — | — |
|  | Polyvinylpyrrolidone vinyl acetate | 0.5 | 0.5 | — | 0.5 | 0.5 |
| Third component | Poloxamer | 0.1 | 0.1 | 0.5 | 0.5 | — |
|  | Polysorbate 80 | — | — | — | — | 0.1 |
|  | Polysorbate 60 | — | — | — | — | — |
|  | Polysorbate 20 | — | — | — | — | — |
| Polyol | Propylene glycol | — | — | 2.5 | 2.5 | 2.5 |
|  | Glycerin | — | — | 2.5 | 2.5 | 2.5 |
| Preservative | Phenoxyethanol | — | — | 0.4 | 0.4 | 0.4 |
|  | Water | Up to 100 | Up to 100 | Up to 100 | Up to 100 | Up to 100 |

| Item | Component | Example 5 wt. %) | Example 6 wt. %) | Example 7 wt. %) | Example 8 wt. %) | Example 9 wt. %) |
|---|---|---|---|---|---|---|
| Drug | (R)-N-[1-(3,5-difluoro-4-methansulfonylamino-phenyl)-ethyl]-3-(2-propyl-6-trifluoromethyl-pyridin-3-yl)-acrylamide | 1 | 1 | 1 | 1 | 1 |
| First component | Microcrystalline cellulose/ Carboxymethylcellulose sodium | 4 | 4 | 4 | 4 | 4 |
| Second component | Hydroxypropyl methylcellulose | — | — | — | — | — |
|  | Polyvinylpyrrolidone vinyl acetate | 0.5 | 0.5 | 0.5 | 0.5 | 0.5 |
| Third component | Poloxamer | — | — | — | — | — |
|  | Polysorbate 80 | — | — | 0.5 | — | — |
|  | Polysorbate 60 | 0.1 | — | — | 0.5 | — |
|  | Polysorbate 20 | — | 0.1 | — | — | 0.5 |
| Polyol | Propylene glycol | 2.5 | 2.5 | 2.5 | 2.5 | 2.5 |
|  | Glycerin | 2.5 | 2.5 | 2.5 | 2.5 | 2.5 |
| Preservative | Phenoxyethanol | 0.4 | 0.4 | 0.4 | 0.4 | 0.4 |
|  | Water | Up to 100 | Up to 100 | Up to 100 | Up to 100 | Up to 100 |

Meanwhile, in order to compare with the composition of one aspect of the present disclosure, Comparative Examples 2 to 12 were prepared by replacing the first component with the components and wt. % as shown in Table 2 below. In Comparative Example 2, the components and wt. % of the drug, the second component and the third component were the same as in Example 1. In Comparative Examples 3 to 12, the rest except for the component and wt. % of the first component were the same as in Example 3.

TABLE 2

| item | Component | wt. % |
|---|---|---|
| Comparative Example 2 | Sodium Carboxymethyl cellulose | 3 |
| Comparative Example 3 | Hydroxyethyl cellulose | 1 |
| Comparative Example 4 | Xanthan gum | 1 |
| Comparative Example 5 | Sodium alginate (LVCR)(viscosity: 100~300 cp(2%, 25° C.); FMC biopolymer company Keltone ® LVCR) | 3 |
| Comparative Example 6 | Sodium alginate (HVCR)(viscosity: 600~900 cp(1.25%, 25° C.); FMC biopolymer company Keltone ® HVCR) | 2 |
| Comparative Example 7 | crosslinked polyacrylic acid (Lubrizol company, Carbomer ® 940 NF) | 0.5 |
| Comparative Example 8 | Methyl cellulose (viscosity: 50 cp) | 3 |
| Comparative Example 9 | Hydropropylcellulose (viscosity: 150~400 cp (2%)) | 4 |
| Comparative Example 10 | Hydropropylcellulose (viscosity: 300~600 cp (10%)) | 4 |
| Comparative Example 11 | Carrageenan | 1 |
| Comparative Example 12 | Colloidal silicon dioxide | 6 |

Experimental Example 1: Evaluation of Sol-Gel Transition, Measurement of Gel Formation Time, Measurement of Viscosity at the Time of Sol or Gel Formation In order to confirm whether the reversible sol-gel transition is achieved, the suspensions of Examples 1 to 9 prepared in Preparation Example 1 and the suspensions of Comparative examples 1 to 12 were visually observed to confirm whether the sol was changed to a gel state (whether gel was formed), and also the time it took (gel formation time) was measured.

Thereafter, only the suspension changed to the gel state was shaken to re-disperse, and after confirming whether it changed to a sol state, it was stored still at isothermal temperature again and the time taken to change to a gel state (gel formation time after redispersing) was measured, and the results are shown in Tables 3 and 4 below. In addition, the viscosity of the suspension in the initial sol state and the viscosity when it changed from the gel to the sol state after redispersing were measured, and the results are shown in Tables 3 and 4 below. In addition, the image obtained by photographing the phenomenon of sol-gel transition for the suspensions of Example 1 and Comparative example 1 is shown in FIG. 1.

TABLE 3

| Evaluation item | Comparative Example 1 | Example 1 | Example 2 | Example 3 | Example 4 | Example 5 | Example 6 | Example 7 | Example 8 | Example 9 |
|---|---|---|---|---|---|---|---|---|---|---|
| Gel formation | X | ○ | ○ | ○ | ○ | ○ | ○ | ○ | ○ | ○ |
| Gel formation time | — | 90 min | 120 min | 120 min | 90 min | 90 min | 90 min | 120 min | 120 min | 120 min |
| Gel formation time after redispersing | — | 110 min | 120 min | 120 min | 120 min | 120 min | 120 min | 120 min | 120 min | 120 min |
| Viscosity (cp) | 133.8 | 434.4 | 514.8 | 447 | 448.8 | 502.2 | 508.2 | 454.8 | 406.8 | 464.4 |
| Viscosity after redispersing (cp) | — | 426.6 | 467.4 | 477.6 | 447 | 403.8 | 447 | 444 | 427.8 | 447.6 |

TABLE 4

| Evaluation item | Comparative Example 2 | Comparative Example 3 | Comparative Example 4 | Comparative Example 5 | Comparative Example 6 | Comparative Example 7 |
|---|---|---|---|---|---|---|
| Gel formation | X | X | X | X | X | X |
| Gel formation time | — | — | — | — | — | — |
| Gel formation time after redispersing | — | — | — | — | — | — |
| Viscosity (cp) | 461.4 | 4314 | 493.8 | 493.8 | 497.6 | Impossible to prepare |
| Viscosity after redispersing (cp) | — | — | — | — | — | Impossible to prepare |

TABLE 4-continued

| Evaluation item | Comparative Example 8 | Comparative Example 9 | Comparative Example 10 | Comparative Example 11 | Comparative Example 12 |
|---|---|---|---|---|---|
| Gel formation | X | X | X | ○ | X |
| Gel formation time | — | — | — | 1 min | — |
| Gel formation time after redispersing | — | — | — | — | — |
| Viscosity (cp) | Impossible to prepare | 143.4 | 10.8 | 59220 | 15 |
| Viscosity after redispersing (cp) | Impossible to prepare | — | — | — | — |

As shown in Tables 3, 4, and FIG. 1, the suspension of Comparative Example 1 did not change to a gel state, and neither of Comparative Examples 2 to 10 and Comparative Example 12 changed to a gel state. Meanwhile, in Comparative Example 11, a gel was formed, but did not change to a sol state after redispersing. On the other hand, it was confirmed that the suspensions of Examples 1 to 9 had a phenomenon of sol-gel transition. In addition, in order to check whether the change from the gel to the sol state occurs by redispersion, the viscosity of the initial sol state and the viscosity after redispersing were compared, and as a result, it was confirmed that they had almost the same viscosity, and thus all the suspensions of Examples 1 to 9 had the viscosity of sol state in the gel state by redispersion.

In addition, it was checked whether a change from a sol state to a gel state occurs by re-dispersing and then leaving for a certain period of time, and as a result, it was confirmed that all the suspensions in Examples 1 to 9 were changed back to a gel state. Accordingly, it was confirmed that the composition enabling reversible sol-gel transition according to one aspect of the present disclosure represents a phenomenon of reversible sol-gel transition.

The invention claimed is:

1. A topical sol-gel composition, comprising
a first component comprising microcrystalline cellulose and carboxymethylcellulose sodium, wherein the first component is contained in an amount of 1 to 10 wt. %, based on the total weight of the topical sol-gel composition;
a second component that is any one selected from the group consisting of hydroxypropyl methylcellulose (HPMC), polyvinylpyrrolidone vinyl acetate (PVP VA), and a mixture thereof; and
a third component that is any one selected from the group consisting of poloxamer, polysorbate, and a mixture thereof, wherein the third component is contained in an amount of 0.5 to 5 wt. % based on a total weight of the sol-gel composition;
wherein the topical sol-gel composition comprises a polyol,
wherein the topical sol-gel composition comprises a drug, wherein the drug is (R)—N-[1-(3,5-difluoro-4-methansulfonylamino-phenyl)-ethyl]-3-(2-propyl-6-trifluoromethyl-pyridin-3-yl)-acrylamide, and
wherein the topical sol gel composition is a reversible sol gel composition that forms a sol state by application of external physical force, and has a viscosity of 50,000 cps in the gel state and a viscosity of 5,000 cps in the sol state, wherein it takes about 110 min to 120 min for formation of the gel state from the sol state when the sol state is left without application of an external physical force.

2. The topical sol-gel composition according to claim 1, wherein the polysorbate is selected from the group consisting of polysorbate 20, polysorbate 60, polysorbate 80, and a combination thereof.

3. The topical sol-gel composition according to claim 1, wherein the polyol is selected from the group consisting of propylene glycol, glycerin, butylene glycol, polyethylene glycol, polypropylene glycol, dipropylene glycol, pentylene glycol, sorbitol, and a combination thereof.

4. The topical sol-gel composition according to claim 1, wherein the topical sol-gel composition further comprises a preservative.

5. The topical sol-gel composition according to claim 4, wherein the preservative is selected from the group consisting of phenoxyethanol, 1,2-hexanediol, 1,3-propanediol, methyl propanediol, 1,2-pentanediol, 1,2-octanediol, 1,2-decanediol, 1,5-pentanediol, 1,6-hexanediol, 1,8-octanediol, 1,2-decanediol, ethylhexylglycerin, hexoxy-propan-1,2-diol, heptoxy-propan-1,2-diol, octoxy-propan-1,2-diol, 3-phenoxy-propan-1,2-diol, 3-benzyloxy-propan-1,2-diol, 3-phenylethyloxy-propan-1,2-diol, 3-phenylpropyloxy-propan-1,2-diol, 3-methylbenzyloxy-propan-1,2-diol, sorbitan caprylate, triclosan, climbazole, Octopirox (1-hydroxy-4-methyl-6-(2,4,4-trimethylpentyl)-2(1H)-pyridone, 2-aminoethanol), chitosan, farnesol, 2-butyloctanoic acid, 2-benzyl-heptan-1-ol, glycerol monolaurate, bis(2-pyridylthio)zinc 1,1'-dioxide, N,N'-(decane-1,10-diyldipyridin-1-yl-4-ylidene)-dioctan-1-amine dihydrochloride (octenidine dihydrochloride), thymol, eugenol, benzyl alcohol, 2-phenyethyl alcohol, 3-phenyl propanol, 1-phenoxy-propan-2-ol, 3-phenoxypropanol, benzyloxymethanol, and a combination thereof.

* * * * *